US011786719B2

(12) United States Patent
Busch et al.

(10) Patent No.: US 11,786,719 B2
(45) Date of Patent: Oct. 17, 2023

(54) ROTARY BLOOD PUMP

(71) Applicant: CARDIACASSIST, INC., Pittsburgh, PA (US)

(72) Inventors: David Busch, Munich (DE); John C. Marous, III, Pittsburgh, PA (US); Anthony S. McCoppin, Blawnox, PA (US); Robert G. Svitek, Freeport, PA (US)

(73) Assignee: CARDIACASSIST, INC., Pittsburgh, PA (US)

( * ) Notice: Subject to any disclaimer, the term of this patent is extended or adjusted under 35 U.S.C. 154(b) by 0 days.

(21) Appl. No.: 17/146,183

(22) Filed: Jan. 11, 2021

(65) Prior Publication Data

US 2021/0128903 A1 May 6, 2021

Related U.S. Application Data

(63) Continuation of application No. PCT/US2019/014685, filed on Jan. 23, 2019.

(Continued)

(51) Int. Cl.
*F04D 7/04* (2006.01)
*A61M 60/232* (2021.01)

(Continued)

(52) U.S. Cl.
CPC ........ *A61M 60/232* (2021.01); *A61M 60/113* (2021.01); *A61M 60/221* (2021.01);

(Continued)

(58) Field of Classification Search
CPC .............. A61M 60/825; A61M 60/818; A61M 60/221; A61M 60/232; A61M 60/422;

(Continued)

(56) References Cited

U.S. PATENT DOCUMENTS 4,507,048 A 3/1985 Belenger et al.
4,994,078 A * 2/1991 Jarvik ................ A61M 60/422 600/16

(Continued)

FOREIGN PATENT DOCUMENTS

CN 103591028 A 2/2014
CN 107347250 A 11/2017

(Continued)

OTHER PUBLICATIONS

International Search Report for International Application No. PCT/US2019/014685, 2 pages, dated Mar. 21, 2019.

(Continued)

*Primary Examiner* — Sabbir Hasan
*Assistant Examiner* — Joshua R Beebe
(74) *Attorney, Agent, or Firm* — Seager, Tufte & Wickhem LLP

(57) ABSTRACT

A centrifugal blood pump includes a housing having a pumping chamber, an inlet having an inlet axis, and an outlet having an outlet axis. The inlet and the outlet are in fluid communication with the pumping chamber. The pump further includes an impeller rotatably disposed within the pumping chamber, and a strut connected to the housing at the inlet. The strut is connected to the housing at a circumferential position about the inlet axis such that a major axis of the strut and the outlet axis define a predetermined angle in a cross-sectional plane perpendicular to the inlet axis. The circumferential position of the strut relative the outlet axis reduces or eliminates damage to blood flowing around the strut.

20 Claims, 8 Drawing Sheets

Related U.S. Application Data

(60) Provisional application No. 62/702,562, filed on Jul. 24, 2018.

(51) Int. Cl.

| | |
|---|---|
| ***A61M 60/221*** | (2021.01) |
| ***A61M 60/422*** | (2021.01) |
| ***F04D 25/06*** | (2006.01) |
| ***F04D 29/046*** | (2006.01) |
| ***F04D 29/42*** | (2006.01) |
| ***A61M 60/814*** | (2021.01) |
| ***A61M 60/825*** | (2021.01) |
| ***A61M 60/113*** | (2021.01) |

(52) U.S. Cl.
CPC ........ *A61M 60/422* (2021.01); *A61M 60/814* (2021.01); *A61M 60/825* (2021.01); *F04D 7/04* (2013.01); *F04D 25/06* (2013.01); *F04D 29/046* (2013.01); *F04D 29/426* (2013.01)

(58) Field of Classification Search
CPC .. A61M 60/82; F04D 29/046; F04D 29/4273; F04D 7/04; F04D 25/06; F04D 29/426
See application file for complete search history.

(56) References Cited

U.S. PATENT DOCUMENTS

| | | | | | |
|---|---|---|---|---|---|
| 5,017,103 | A | | 5/1991 | Dahl | |
| 5,360,317 | A | * | 11/1994 | Clausen | F04D 13/026 415/206 |
| 5,399,074 | A | * | 3/1995 | Nose | A61M 60/419 417/423.12 |
| 5,746,575 | A | * | 5/1998 | Westphal | A61M 60/812 415/206 |
| 5,840,070 | A | * | 11/1998 | Wampler | H02K 41/03 417/423.1 |
| 5,895,203 | A | * | 4/1999 | Klein | F04D 13/026 415/142 |
| 5,957,672 | A | * | 9/1999 | Aber | A61M 60/237 417/423.12 |
| 6,018,208 | A | * | 1/2000 | Maher | H02K 15/0006 417/423.1 |
| 6,093,001 | A | * | 7/2000 | Burgreen | A61M 60/422 415/176 |
| 6,186,665 | B1 | * | 2/2001 | Maher | F04D 29/0467 417/423.12 |
| 6,234,772 | B1 | | 5/2001 | Wampler et al. | |
| 6,254,359 | B1 | * | 7/2001 | Aber | F04D 13/0633 417/423.12 |
| 6,527,699 | B1 | * | 3/2003 | Goldowsky | A61M 60/825 600/16 |
| 7,762,941 | B2 | * | 7/2010 | Jarvik | F04D 13/0633 600/16 |
| 7,959,551 | B2 | * | 6/2011 | Jarvik | F04D 3/00 600/16 |
| 8,088,059 | B2 | * | 1/2012 | Jarvik | F04D 29/0467 600/16 |
| 8,801,405 | B2 | * | 8/2014 | Hoshi | F04D 29/0467 416/182 |
| 9,162,018 | B2 | * | 10/2015 | Foster | A61M 60/205 |
| 10,724,534 | B2 | * | 7/2020 | Woo | F04D 29/24 |
| 10,773,002 | B2 | * | 9/2020 | Siess | A61M 60/205 |
| 10,890,190 | B2 | * | 1/2021 | Kawai | F04D 13/0606 |
| 2014/0205434 | A1 | | 7/2014 | Graichen et al. | |
| 2015/0038769 | A1 | | 2/2015 | LaRose et al. | |
| 2017/0143884 | A1 | | 5/2017 | Tanaka et al. | |
| 2017/0234314 | A1 | * | 8/2017 | Ehrsam | F16C 23/048 417/423.7 |
| 2020/0368415 | A1 | * | 11/2020 | Antaki | A61M 60/422 |

FOREIGN PATENT DOCUMENTS

| | | | | | |
|---|---|---|---|---|---|
| CN | 107921187 | A | | 4/2018 | |
| DE | 19626224 | A1 | | 1/1998 | |
| EP | 3826695 | A1 | | 6/2021 | |
| JP | H07136247 | A | | 5/1995 | |
| JP | H08501366 | A | | 2/1996 | |
| JP | 2009523488 | A | | 6/2009 | |
| WO | 9403731 | A1 | | 2/1994 | |
| WO | 2007084339 | A2 | | 7/2007 | |
| WO | WO-2016146661 | A1 | * | 9/2016 | A61M 60/135 |
| WO | 2017164599 | A1 | | 9/2017 | |

OTHER PUBLICATIONS

Written Opinion for International Application No. PCT/US2019/014685, 6 pages, dated Mar. 21, 2019.

Extended European Search Report for Application No. EP19841877.4 dated Mar. 18, 2022.

* cited by examiner

ROTARY BLOOD PUMP

CROSS-REFERENCE TO RELATED APPLICATIONS

This application is a continuation of International Application No. PCT/US2019/014685, filed Jan. 23, 2019, which claims priority to U.S. Provisional Application No. 62/702,562, filed on Jul. 24, 2018, the disclosures of which are hereby incorporated by reference in its entirety.

BACKGROUND OF THE DISCLOSURE

Field of the Disclosure

The present disclosure is generally related to a rotary blood pump, and, in particular, to a rotary blood pump having a bearing mechanism for supporting an impeller within a pumping chamber and a drive mechanism for rotatably driving the impeller within the pumping chamber.

Description of Related Art

Rotary blood pumps have long been used with assisting or supplementing the function of a human heart. For example, rotary blood pumps assist heart function due to a damaged left ventricle, or for temporary heart bypass during cardiac surgery. In general, a rotary blood pump has an impeller disposed within a pumping chamber of a pump housing. Blood is delivered via an axial inlet of the housing and is pumped by the impeller to a radial outlet. The impeller is rotatably driven within the pumping chamber by a drive mechanism, such as a drive magnet in the impeller that is rotatably driven by an electromagnet in the housing.

Due to high rotating speeds of the impeller during pump operation (2,000 to 7,500 rpm), the impeller must be adequately supported within the pump housing to prevent damage to the blood cells due to shearing or flow stagnation. In some existing pump designs, the impeller is fully magnetically suspended within the pumping chamber. Such impeller support systems often require complex control of the magnets used for suspending the impeller. In other designs, the impeller may be hydrodynamically suspended within the pumping chamber, where hydrodynamic force of blood within the pumping chamber is used to support the impeller and prevent the impeller from contacting the sidewalls of the pumping chamber. With hydrodynamic impeller support, the impeller is often free to contact the sidewalls of the pumping chamber during pump startup until a sufficient fluid pressure is built. As a result, blood cells may be damaged during pump startup. Some rotary blood pumps have a fully mechanical bearing supporting the impeller within the pump housing. A disadvantage of mechanical bearings is that they may transfer heat to the blood and may result in blood clotting.

In view of these and other disadvantages of conventional rotary blood pumps, there is a need in the art for improved rotary blood pumps having a bearing mechanism for supporting the impeller in a manner that overcomes the shortcomings of existing rotary blood pumps.

SUMMARY OF THE DISCLOSURE

The present disclosure is generally related to a rotary blood pump, and, in particular, to a rotary blood pump having a bearing mechanism for supporting an impeller within a pumping chamber, and a drive mechanism for rotatably driving the impeller within the pumping chamber.

In some examples of the present disclosure, a centrifugal blood pump may have a housing having a pumping chamber, an inlet with an inlet axis, and an outlet with an outlet axis, the inlet and the outlet being in fluid communication with the pumping chamber. The pump may further have an impeller rotatably disposed within the pumping chamber, and a strut connected to the housing at the inlet. The strut may be connected to the housing at a circumferential position about the inlet axis such that a major axis of the strut and the outlet axis define a predetermined angle in a cross-sectional plane perpendicular to the inlet axis. The circumferential position of the strut relative the outlet axis may reduce thrombosis of blood flowing around the strut.

In other examples of the present disclosure, the strut may have a single connection point with the housing in the cross-sectional plane perpendicular to the inlet axis. The predetermined angle may be about 15° to about 75°, such as about 45°. At least a portion of the strut may have a teardrop cross-sectional shape. The impeller may have at least one passage defining a secondary flow path. The at least one passage may be substantially perpendicular to the outlet axis. During operation of the blood pump, the impeller may deliver a first portion of blood flow from the inlet directly to the outlet, and may deliver a second portion of the blood flow from the inlet to the outlet via the at least one passage.

In other examples of the present disclosure, a bearing mechanism for supporting the impeller within the pumping chamber may include a radial bearing having a first permanent magnet associated with the impeller and a second permanent magnet associated with the housing. The first permanent magnet may magnetically interact with the second permanent magnet to radially position the impeller within the pumping chamber. The bearing mechanism further may have an axial bearing comprising a first bearing element associated with the impeller and a second bearing element connected to the strut.

In other examples of the present disclosure, the impeller may have at least one passage defining a secondary flow path such that, during operation of the blood pump, the impeller delivers a first portion of blood flow from the inlet directly to the outlet, and delivers a second portion of the blood flow from the inlet to the outlet via the secondary flow path to cool the axial bearing. The first bearing element may be ball-shaped and the second bearing element may be cup-shaped to receive at least a portion of the ball-shaped first bearing element. Alternatively, the second bearing element may be ball-shaped and the first bearing element may be cup-shaped to receive at least a portion of the ball-shaped second bearing element. The first bearing element may be a jewel bearing. The second bearing element may be made from a ceramic material. The first permanent magnet may be axially offset relative to the second permanent magnet by a predetermined distance to urge the impeller in a direction toward the inlet with a predetermined axial force. A motor mechanism for rotating the impeller within the pumping chamber may have a permanent magnet rotor associated with the impeller and an electromagnetic coil stator associated with the housing.

In other examples of the present disclosure, a centrifugal blood pump may have a housing having a pumping chamber, an inlet with an inlet axis, and an outlet with an outlet axis, the inlet and the outlet being in fluid communication with the pumping chamber. The pump may further have an impeller rotatably disposed within the pumping chamber and having at least one passage defining a secondary flow path, a bearing mechanism supporting the impeller within the pumping chamber, and a strut connected to the housing at the inlet to support at least a portion of the bearing mechanism. The strut may be connected to the housing at a circumferential position about the inlet axis such that a major axis of the strut and the outlet axis define a predetermined angle in a cross-sectional plane perpendicular to the inlet axis. The circumferential position of the strut relative to the outlet axis may reduce thrombosis of blood flowing around the strut.

In other examples of the present disclosure, the strut may have a single connection point with the housing in the cross-sectional plane perpendicular to the inlet axis. The predetermined angle may be about 15° to about 75°, such as about 45°. At least a portion of the strut may have a teardrop cross-sectional shape. The at least one passage defining the secondary flow path may be substantially perpendicular to the outlet axis. During operation of the blood pump, the impeller may deliver a first portion of blood flow from the inlet directly to the outlet, and may deliver a second portion of the blood flow from the inlet to the outlet via the at least one passage.

In other examples of the present disclosure, the bearing mechanism may have a radial bearing having a first permanent magnet associated with the impeller and a second permanent magnet associated with the housing. The first permanent magnet may magnetically interact with the second permanent magnet to radially position the impeller within the pumping chamber. The bearing mechanism may further have an axial bearing having a first bearing element associated with the impeller and a second bearing element connected to the strut. During operation of the blood pump, the impeller may deliver a first portion of blood flow from the inlet directly to the outlet, and may deliver a second portion of the blood flow from the inlet to the outlet via the secondary flow path to cool the axial bearing. The first bearing element may be ball-shaped and the second bearing element may be cup-shaped to receive at least a portion of the ball-shaped first bearing element. Alternatively, the second bearing element may be ball-shaped and the first bearing element may be cup-shaped to receive at least a portion of the ball-shaped second bearing element. The first bearing element may be a jewel bearing. The second bearing element may be made from a ceramic material. The first permanent magnet may be axially offset relative to the second permanent magnet by a predetermined distance to urge the impeller in a direction toward the inlet with a predetermined axial force.

In other examples of the present disclosure, a centrifugal blood pump may have a housing having a pumping chamber, an inlet with an inlet axis, and an outlet with an outlet axis, the inlet and the outlet being in fluid communication with the pumping chamber. The pump may further have an impeller rotatably disposed within the pumping chamber, and a bearing mechanism for supporting the impeller within the pumping chamber. The bearing mechanism may have a radial bearing having a first permanent magnet associated with the impeller and a second permanent magnet associated with the housing. The first permanent magnet may magnetically interact with the second permanent magnet to radially position the impeller within the pumping chamber. The bearing mechanism may further have an axial bearing having a first bearing element associated with the impeller and a second bearing element associated with a strut connected to the housing at the inlet. The first permanent magnet may be axially offset relative to the second permanent magnet by a predetermined distance to urge the impeller in a direction toward the inlet with a predetermined axial force.

In other examples of the present disclosure, the first bearing element may be ball-shaped and the second bearing element may be cup-shaped to receive at least a portion of the ball-shaped first bearing element. Alternatively, the second bearing element may be ball-shaped and the first bearing element may be cup-shaped to receive at least a portion of the ball-shaped second bearing element. The first bearing element may be a jewel bearing. The second bearing element may be made from a ceramic material.

In other examples of the present disclosure, a centrifugal blood pump may have a housing having a pumping chamber, an inlet with an inlet axis, and an outlet with an outlet axis, the inlet and the outlet in fluid communication with the pumping chamber. The pump may have an impeller rotatably disposed within the pumping chamber, and a bearing mechanism for supporting the impeller within the pumping chamber. The bearing mechanism may have a radial bearing having a first permanent magnet associated with the impeller and a second permanent magnet associated with the housing. The first permanent magnet may magnetically interact with the second permanent magnet to radially position the impeller within the pumping chamber. The bearing mechanism may further have an axial bearing having a first bearing element associated with the impeller and a second bearing element associated with a strut connected to the housing at the inlet. The strut may be connected to the housing at a circumferential position about the inlet axis such that a major axis of the strut and the outlet axis define a predetermined angle in a cross-sectional plane perpendicular to the inlet axis. The circumferential position of the strut relative to the outlet axis may reduce or eliminate damage to blood flowing around the strut.

In other examples of the present disclosure, the strut may have a single connection point with the housing in the cross-sectional plane perpendicular to the inlet axis. The predetermined angle may be about 15° to about 75°, such as about 45°. At least a portion of the strut may have a teardrop cross-sectional shape. The impeller may have at least one passage defining a secondary flow path. The at least one passage may be substantially perpendicular to the outlet axis. During operation of the blood pump, the impeller may deliver a first portion of blood flow from the inlet directly to the outlet, and may deliver a second portion of the blood flow from the inlet to the outlet via the at least one passage.

In other examples of the present disclosure, the pump has a motor mechanism for rotating the impeller within the pumping chamber. The motor mechanism may have a permanent magnet rotor associated with the impeller and an electromagnetic coil stator associated with the housing. The first bearing element may be ball-shaped and the second bearing element may be cup-shaped to receive at least a portion of the ball-shaped first bearing element. Alternatively, the second bearing element may be ball-shaped and the first bearing element may be cup-shaped to receive at least a portion of the ball-shaped second bearing element. The first bearing element may be a jewel bearing. The second bearing element may be made from a ceramic material.

In other examples of the present disclosure, a centrifugal blood pump may have a housing having a pumping chamber, an inlet having an inlet axis, and an outlet having an outlet axis, the inlet and the outlet in fluid communication with the pumping chamber. The pump may also have an impeller rotatably disposed within the pumping chamber, and a bearing mechanism for supporting the impeller within the pumping chamber. The bearing mechanism may have a radial bearing having a first permanent magnet associated with the impeller and a second permanent magnet associated with the housing. The first permanent magnet may magnetically interact with the second permanent magnet to radially position the impeller within the pumping chamber. The bearing mechanism may further have an axial bearing with a first bearing element associated with the impeller and a second bearing element associated with a strut connected to the housing at the inlet. The strut may have a single connection point with the housing in a cross-sectional plane perpendicular to the inlet axis.

In other examples of the present disclosure, the strut may be connected to the housing at a circumferential position about the inlet axis such that a major axis of the strut and the outlet axis define a predetermined angle in the cross-sectional plane perpendicular to the inlet axis. The predetermined angle may be about 15° to about 75°, such as about 45°. At least a portion of the strut may have a teardrop cross-sectional shape. The impeller may have at least one passage defining a secondary flow path. The at least one passage may be substantially perpendicular to the outlet axis. During operation of the blood pump, the impeller may deliver a first portion of blood flow from the inlet directly to the outlet, and may deliver a second portion of the blood flow from the inlet to the outlet via the at least one passage. The first bearing element may be ball-shaped and the second bearing element may be cup-shaped to receive at least a portion of the ball-shaped first bearing element. Alternatively, the second bearing element may be ball-shaped and the first bearing element may be cup-shaped to receive at least a portion of the ball-shaped second bearing element. The first bearing element may be a jewel bearing. The second bearing element may be made from a ceramic material. The first permanent magnet may be axially offset relative to the second permanent magnet by a predetermined distance to urge the impeller in a direction toward the inlet with a predetermined axial force.

In other examples of the present disclosure, a bearing mechanism for supporting an impeller within a housing of a centrifugal blood pump may have a radial bearing having a first permanent magnet configured for mounting on the impeller and a second permanent magnet configured for mounting on the housing. The first permanent magnet may magnetically interact with the second permanent magnet to radially position the impeller within the housing. The first permanent magnet may be axially offset relative to the second permanent magnet to urge the impeller axially with a predetermined axial force. The bearing mechanism may further have an axial bearing having a first bearing element configured for mounting on the impeller and a second bearing element mounted on a strut configured for connecting to at least a portion of the housing. The axial bearing may be configured to counteract the predetermined axial force. The strut may have a single attachment point on the housing in a cross-sectional plane of the housing.

In other examples of the present disclosure, the first bearing element may be ball-shaped and the second bearing element may be cup-shaped to receive at least a portion of the ball-shaped first bearing element. Alternatively, the second bearing element may be ball-shaped and the first bearing element may be cup-shaped to receive at least a portion of the ball-shaped second bearing element. The first bearing element may be a jewel bearing. The second bearing element may be made from a ceramic material.

Various other aspects of the present invention are recited in one or more of the following clauses:

Clause 1. A centrifugal blood pump comprising: a housing having a pumping chamber, an inlet with an inlet axis, and an outlet with an outlet axis, the inlet and the outlet being in fluid communication with the pumping chamber; an impeller rotatably disposed within the pumping chamber; and a strut connected to the housing at the inlet, wherein the strut is connected to the housing at a circumferential position about the inlet axis such that a major axis of the strut and the outlet axis define a predetermined angle in a cross-sectional plane perpendicular to the inlet axis, and wherein the circumferential position of the strut relative the outlet axis reduces or eliminates damage to blood flowing around the strut.

Clause 2. The centrifugal blood pump of clause 1, wherein the strut has a single connection point with the housing in the cross-sectional plane perpendicular to the inlet axis.

Clause 3: The centrifugal blood pump of clauses 1 or 2, wherein the predetermined angle is about 15° to about 75°, such as about 45°.

Clause 4. The centrifugal blood pump of any of clauses 1-3, wherein at least a portion of the strut has a teardrop cross-sectional shape.

Clause 5. The centrifugal blood pump of any of clauses 1-4, wherein the impeller has at least one passage defining a secondary flow path.

Clause 6. The centrifugal blood pump of clause 5, wherein the at least one passage is substantially perpendicular to the outlet axis.

Clause 7. The centrifugal blood pump of clauses 5 or 6, wherein, during operation of the blood pump, the impeller delivers a first portion of blood flow from the inlet directly to the outlet, and delivers a second portion of the blood flow from the inlet to the outlet via the at least one passage.

Clause 8. The centrifugal blood pump of any of clauses 1-7, further comprising a bearing mechanism supporting the impeller within the pumping chamber, the bearing mechanism comprising: a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first bearing element associated with the impeller and a second bearing element connected to the strut.

Clause 9. The centrifugal blood pump of clause 8, wherein the impeller has at least one passage defining a secondary flow path such that, during operation of the blood pump, the impeller delivers a first portion of blood flow from the inlet directly to the outlet, and delivers a second portion of the blood flow from the inlet to the outlet via the secondary flow path to cool the axial bearing.

Clause 10. The centrifugal blood pump of clauses 8 or 9, wherein the first bearing element is ball-shaped and the second bearing element is cup-shaped to receive at least a portion of the ball-shaped first bearing element or wherein the second bearing element is ball-shaped and the first bearing element is cup-shaped to receive at least a portion of the ball-shaped second bearing element.

Clause 11. The centrifugal blood pump of any of clauses 8-10, wherein the first bearing element is a jewel bearing.

Clause 12. The centrifugal blood pump of any of clauses 8-11, wherein the second bearing element is made from a ceramic material.

Clause 13. The centrifugal blood pump of any of clauses 8-12, wherein the first permanent magnet is axially offset relative to the second permanent magnet by a predetermined distance to urge the impeller in a direction toward the inlet with a predetermined axial force.

Clause 14. The centrifugal blood pump of any of clauses 1-13, further comprising a motor mechanism for rotating the impeller within the pumping chamber, the motor mechanism having a permanent magnet rotor associated with the impeller and an electromagnetic coil stator associated with the housing.

Clause 15. A centrifugal blood pump comprising: a housing having a pumping chamber, an inlet with an inlet axis, and an outlet with an outlet axis, the inlet and the outlet being in fluid communication with the pumping chamber; an impeller rotatably disposed within the pumping chamber and having at least one passage defining a secondary flow path; a bearing mechanism supporting the impeller within the pumping chamber; and a strut connected to the housing at the inlet to support at least a portion of the bearing mechanism, wherein the strut is connected to the housing at a circumferential position about the inlet axis such that the strut and the outlet axis define a predetermined angle in a cross-sectional plane perpendicular to the inlet axis, and wherein the circumferential position of the strut relative the outlet axis reduces or eliminates damage to blood flowing around the strut.

Clause 16. The centrifugal blood pump of clause 15, wherein the strut has a single connection point with the housing in the cross-sectional plane perpendicular to the inlet axis.

Clause 17. The centrifugal blood pump of clauses 15 or 16, wherein the predetermined angle is about 15° to about 75°, such as about 45°.

Clause 18. The centrifugal blood pump of any of clauses 15-17, wherein at least a portion of the strut has a teardrop cross-sectional shape.

Clause 19. The centrifugal blood pump of any of clauses 15-18, wherein the at least one passage defining the secondary flow path is substantially perpendicular to the outlet axis.

Clause 20. The centrifugal blood pump of any of clauses 15-19, wherein, during operation of the blood pump, the impeller delivers a first portion of blood flow from the inlet directly to the outlet, and delivers a second portion of the blood flow from the inlet to the outlet via the at least one passage.

Clause 21. The centrifugal blood pump of any of clauses 15-20, the bearing mechanism comprising: a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first bearing element associated with the impeller and a second bearing element connected to the strut.

Clause 22. The centrifugal blood pump of clause 21, wherein, during operation of the blood pump, the impeller delivers a first portion of blood flow from the inlet directly to the outlet, and delivers a second portion of the blood flow from the inlet to the outlet via the secondary flow path to cool the axial bearing.

Clause 23. The centrifugal blood pump of clauses 21 or 22, wherein the first bearing element is ball-shaped and the second bearing element is cup-shaped to receive at least a portion of the ball-shaped first bearing element or wherein the second bearing element is ball-shaped and the first bearing element is cup-shaped to receive at least a portion of the ball-shaped second bearing element.

Clause 24. The centrifugal blood pump of any of clauses 21-23, wherein the first Clause 25. The centrifugal blood pump of any of clauses 21-24, wherein the second bearing element is made from a ceramic material.

Clause 26. The centrifugal blood pump of any of clauses 21-25, wherein the first permanent magnet is axially offset relative to the second permanent magnet by a predetermined distance to urge the impeller in a direction toward the inlet with a predetermined axial force.

Clause 27. A centrifugal blood pump comprising: a housing having a pumping chamber, an inlet with an inlet axis, and an outlet with an outlet axis, the inlet and the outlet being in fluid communication with the pumping chamber; an impeller rotatably disposed within the pumping chamber; and a bearing mechanism for supporting the impeller within the pumping chamber, the bearing mechanism comprising: a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first bearing element associated with the impeller and a second bearing element associated with a strut connected to the housing at the inlet, wherein the first permanent magnet is axially offset relative to the second permanent magnet by a predetermined distance to urge the impeller in a direction toward the inlet with a predetermined axial force.

Clause 28. The centrifugal blood pump of clause 27, wherein the first bearing element is ball-shaped and the second bearing element is cup-shaped to receive at least a portion of the ball-shaped first bearing element or wherein the second bearing element is ball-shaped and the first bearing element is cup-shaped to receive at least a portion of the ball-shaped second bearing element.

Clause 29. The centrifugal blood pump of clauses 27-28, wherein the first bearing element is a jewel bearing.

Clause 30. The centrifugal blood pump of any of clauses 27-29, wherein the second bearing element is made from a ceramic material.

Clause 31. A centrifugal blood pump comprising: a housing having a pumping chamber, an inlet with an inlet axis, and an outlet with an outlet axis, the inlet and the outlet in fluid communication with the pumping chamber; an impeller rotatably disposed within the pumping chamber; and a bearing mechanism for supporting the impeller within the pumping chamber, the bearing mechanism comprising: a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first bearing element associated with the impeller and a second bearing element associated with a strut connected to the housing at the inlet, wherein the strut is connected to the housing at a circumferential position about the inlet axis such that a major axis of the strut and the outlet axis define a predetermined angle in a cross-sectional plane perpendicular to the inlet axis, and wherein the circumferential position of the strut relative to the outlet axis reduces or eliminates damage to blood flowing around the strut.

Clause 32. The centrifugal blood pump of clause 31, wherein the strut has a single connection point with the housing in the cross-sectional plane perpendicular to the inlet axis.

Clause 33. The centrifugal blood pump of clauses 31 or 32, wherein the predetermined angle is about 15° to about 75°, such as about 45°.

Clause 34. The centrifugal blood pump of any of clauses 31-33, wherein at least a portion of the strut has a teardrop cross-sectional shape.

Clause 35. The centrifugal blood pump of any of clauses 31-34, wherein the impeller has at least one passage defining a secondary flow path.

Clause 36. The centrifugal blood pump of any of clauses 31-35, wherein the at least one passage substantially perpendicular to the outlet axis.

Clause 37. The centrifugal blood pump of any of clauses 31-36, wherein during operation of the blood pump, the impeller delivers a first portion of blood flow from the inlet directly to the outlet, and delivers a second portion of the blood flow from the inlet to the outlet via the at least one passage.

Clause 38. The centrifugal blood pump of any of clauses 31-37, further comprising a motor mechanism for rotating the impeller within the pumping chamber, the motor mechanism having a permanent magnet rotor associated with the impeller and an electromagnetic coil stator associated with the housing.

Clause 39. The centrifugal blood pump of any of clauses 31-38, wherein the first bearing element is ball-shaped and wherein the second bearing element is cup-shaped to receive at least a portion of the ball-shaped first bearing element.

Clause 40. The centrifugal blood pump of any of clauses 31-39, wherein the second bearing element is ball-shaped and wherein the first bearing element is cup-shaped to receive at least a portion of the ball-shaped second bearing element.

Clause 41. The centrifugal blood pump of any of clauses 31-40, wherein the first bearing element is a jewel bearing.

Clause 42. The centrifugal blood pump of any of clauses 31-41, wherein the second bearing element is made from a ceramic material.

Clause 43. A centrifugal blood pump comprising: a housing having a pumping chamber, an inlet having an inlet axis, and an outlet having an outlet axis, the inlet and the outlet in fluid communication with the pumping chamber; an impeller rotatably disposed within the pumping chamber; and a bearing mechanism for supporting the impeller within the pumping chamber, the bearing mechanism comprising: a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first bearing element associated with the impeller and a second bearing element associated with a strut connected to the housing at the inlet, wherein the strut has a single connection point with the housing in a cross-sectional plane perpendicular to the inlet axis.

Clause 44. The centrifugal blood pump of clause 43, wherein the strut is connected to the housing at a circumferential position about the inlet axis such that a major axis of the strut and the outlet axis define a predetermined angle in the cross-sectional plane perpendicular to the inlet axis.

Clause 45. The centrifugal blood pump of clauses 43 or 44, wherein the predetermined angle is about 15° to about 75°, such as about 45°.

Clause 46. The centrifugal blood pump of any of clauses 43-45, wherein at least a portion of the strut has a teardrop cross-sectional shape.

Clause 47. The centrifugal blood pump of any of clauses 43-46, wherein the impeller has at least one passage defining a secondary flow path.

Clause 48. The centrifugal blood pump of clause 47, wherein the at least one passage is substantially perpendicular to the outlet axis.

Clause 49. The centrifugal blood pump of clauses 47 or 48, wherein, during operation of the blood pump, the impeller delivers a first portion of blood flow from the inlet directly to the outlet, and delivers a second portion of the blood flow from the inlet to the outlet via the at least one passage.

Clause 50. The centrifugal blood pump of any of clauses 43-49, wherein the first bearing element is ball-shaped and wherein the second bearing element is cup-shaped to receive at least a portion of the ball-shaped first bearing element.

Clause 51. The centrifugal blood pump of any of clauses 43-50, wherein the second bearing element is ball-shaped and wherein the first bearing element is cup-shaped to receive at least a portion of the ball-shaped second bearing element.

Clause 52. The centrifugal blood pump of any of clauses 43-51, wherein the first bearing element is a jewel bearing.

Clause 53. The centrifugal blood pump of any of clauses 43-52, wherein the second bearing element is made from a ceramic material.

Clause 54. The centrifugal blood pump of any of clauses 43-53, wherein the first permanent magnet is axially offset relative to the second permanent magnet by a predetermined distance to urge the impeller in a direction toward the inlet with a predetermined axial force.

Clause 55. A bearing mechanism for supporting an impeller within a housing of a centrifugal blood pump, the bearing mechanism comprising: a radial bearing having a first permanent magnet configured for mounting on the impeller and a second permanent magnet configured for mounting on the housing, wherein the first permanent magnet magnetically interacts with the second permanent magnet to radially position the impeller within the housing, and wherein the first permanent magnet is axially offset relative to the second permanent magnet to urge the impeller axially with a predetermined axial force; and an axial bearing having a first bearing element configured for mounting on the impeller and a second bearing element mounted on a strut configured for connecting to at least a portion of the housing, wherein the axial bearing is configured to counteract the predetermined axial force, and wherein the strut has a single attachment point on the housing in a cross-sectional plane of the housing.

Clause 56. The bearing mechanism of clause 55, wherein the first bearing element is ball-shaped and wherein the second bearing element is cup-shaped to receive at least a portion of the ball-shaped first bearing element.

Clause 57. The bearing mechanism of clauses 55 or 56, wherein the second bearing element is ball-shaped and wherein the first bearing element is cup-shaped to receive at least a portion of the ball-shaped second bearing element.

Clause 58. The bearing mechanism of any of clauses 55-57, wherein the first bearing element is a jewel bearing.

Clause 59. The bearing mechanism of any of clauses 55-58, wherein the second bearing element is made from a ceramic material.

Further details and advantages of the various examples described in detail herein will become clear upon reviewing the following detailed description of the various examples in conjunction with the accompanying drawing figures.

DETAILED DESCRIPTION OF THE INVENTION

Figure 1:
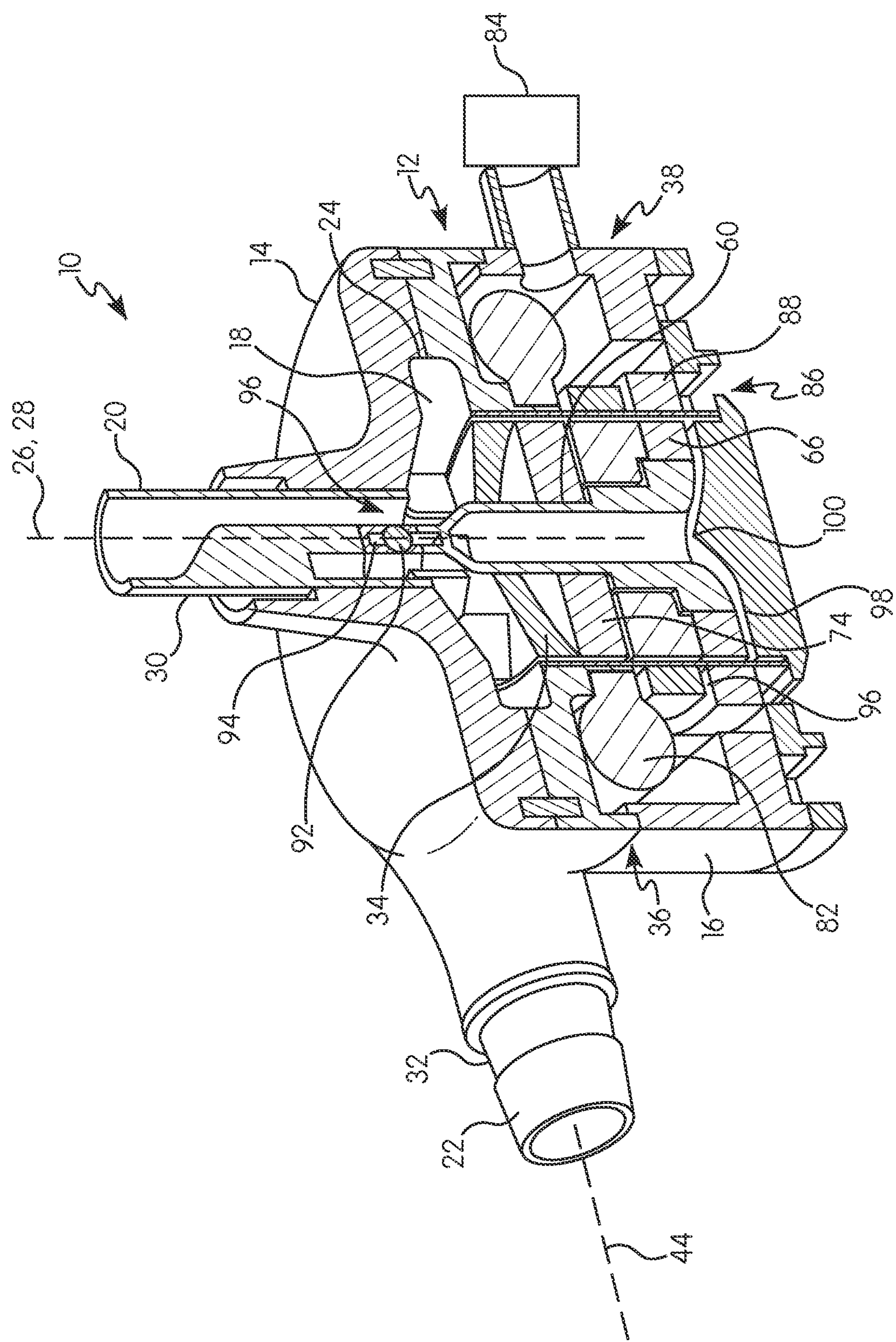
FIG. 1 is a front, perspective cross-sectional view of a rotary blood pump in accordance with one example of the present disclosure.

The illustrations generally show preferred and non-limiting examples of the apparatus and methods of the present disclosure. While the description presents various aspects of the apparatus, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

The following description is provided to enable those skilled in the art to make and use the described examples contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

As used herein, the term "substantially parallel" means a relative angle as between two objects (if extended to theoretical intersection), such as elongated objects and including reference lines, that is from 0° to 5°, or from 0° to 3°, or from 0° to 2°, or from 0° to 1°, or from 0° to 0.5°, or from 0° to 0.25°, or from 0° to 0.1°, inclusive of the recited values.

As used herein, the term "substantially perpendicular" means a relative angle as between two objects (if extended to theoretical intersection), such as elongated objects and including reference lines, that is from 85° to 90°, or from 87° to 90°, or from 88° to 90°, or from 89° to 90°, or from 89.5° to 90°, or from 89.75° to 90°, or from 89.9° to 90°, inclusive of the recited values.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

It should be understood that any numerical range recited herein is intended to include all sub-ranges subsumed therein. For example, a range of "1 to 10" is intended to include all subranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances. Further, in this application, the use of "a" or "an" means "at least one" unless specifically stated otherwise. The term "at least" is synonymous with "greater than or equal to". As used herein, "at least one of is synonymous with "one or more of. For example, the phrase "at least one of A, B, and C" means any one of A, B, or C, or any combination of any two or more of A, B, or C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C.

Figure 2:
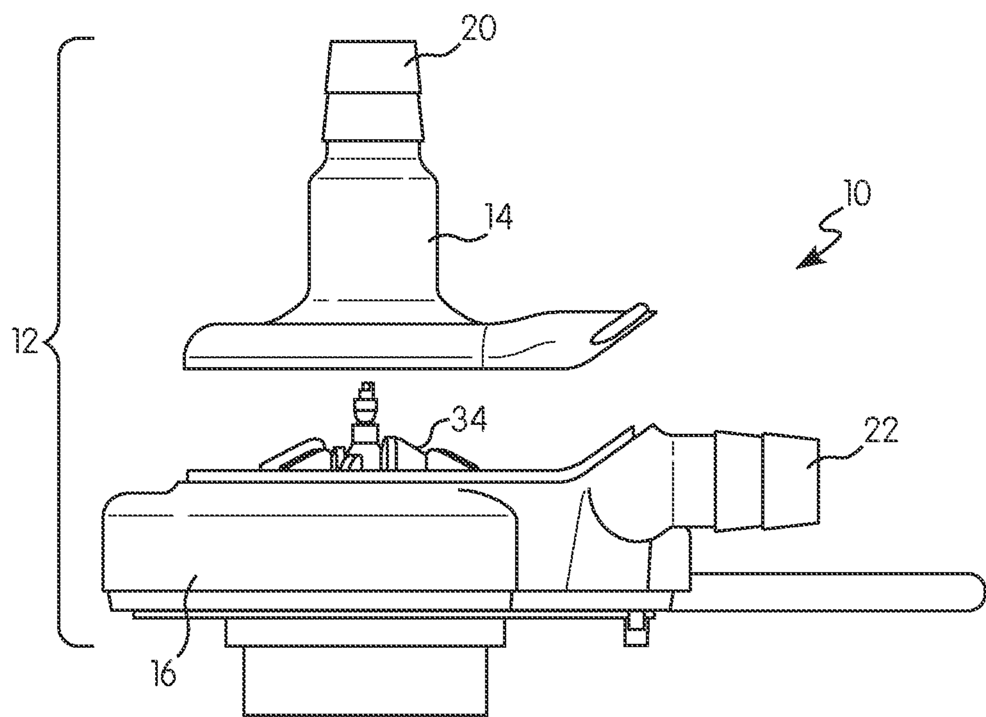
FIG. 2 is an exploded side view of the rotary blood pump shown in FIG. 1 shown without a lower housing portion.

Referring to the drawings, in which like reference characters refer to the like parts throughout the several views thereof, FIG. 1 illustrates a rotary blood pump 10 in accordance with one example of the present invention. The rotary blood pump 10 may be used, for example, in an extracorporeal circuit for supporting the function of a patient's heart and/or lungs. Generally, the rotary blood pump 10 has a pump housing 12 with an upper or inlet housing portion 14 and a lower or outlet housing portion 16. The inlet housing portion 14 and the outlet housing portion 16 may be removably or non-removably coupled together and define a pumping chamber 18 therebetween. In some examples, the inlet housing portion 14 is formed as a separate component that is removably or non-removably secured to the outlet housing portion 16 (see FIG. 2). The pumping chamber 18 may have a substantially cylindrical structure defined by a sidewall 24 extending circumferentially around a central longitudinal axis 26.

With continued reference to FIG. 1, the inlet housing portion 14 has an inlet 20 that is in fluid communication with the pumping chamber 18 for delivering blood into the pumping chamber 18. The inlet 20 has a tubular shape with an inlet axis 42 that is substantially parallel with the central longitudinal axis 26 of the pumping chamber 18. The inlet 20 may have a circular cross-sectional shape, an oval cross-sectional shape, or any other geometric shape, such as polygonal. In some examples, the inlet axis 42 may be angled relative to the central longitudinal axis 26. The inlet axis 42 may be substantially coaxial with the central longitudinal axis 26. In some examples, the inlet axis 42 may be offset radially relative to the central longitudinal axis 26. The inlet 20 has one or more barbs 30 or other connection elements to facilitate connecting with an inlet tube (not shown).

With continued reference to FIG. 1, the outlet housing portion 16 has an outlet 22 in fluid communication with the pumping chamber 18 for delivering blood from the pumping chamber 18. The outlet 22 has a tubular shape with an outlet axis 44 that is substantially perpendicular relative to the central longitudinal axis 26 of the pumping chamber 18. The outlet 22 may have a circular cross-sectional shape, an oval cross-sectional shape, or any other geometric shape, such as polygonal. In some examples, the outlet axis 44 may be angled relative to the central longitudinal axis 26 and/or the inlet axis 42. The outlet 22 has one or more barbs 30 or other connection elements to facilitate connecting with an outlet tube (not shown).

With continued reference to FIG. 1, an impeller 34 is rotatably supported within the pumping chamber 18 and is configured for pumping blood from the inlet 20 to the outlet 22. The impeller 34 is rotatably driven by a drive mechanism 36. As described herein, the drive mechanism 36 is configured to rotate the impeller 34 about the central longitudinal axis 26 such that the impeller 34 pumps blood from the inlet 20 to the outlet 22. The impeller 34 is rotatably supported within the pumping chamber 18 by a bearing mechanism 38. As described herein, the bearing mechanism 38 assists in positioning the impeller 34 within the pumping chamber 18 such that the impeller 34 rotates about the central longitudinal axis 26 without touching the sidewall 24 of the pumping chamber 18.

Figure 3:
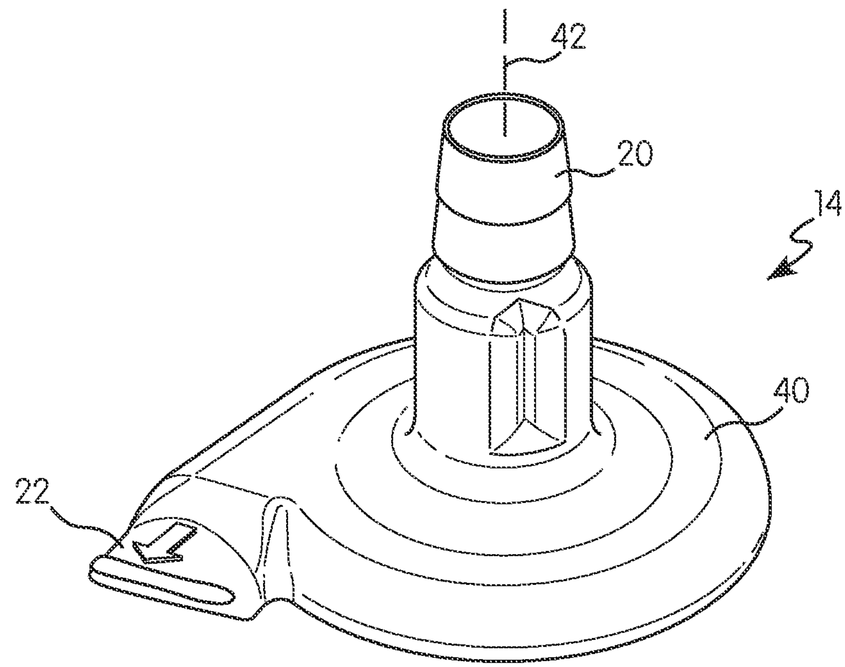
FIG. 3 is a perspective view of an inlet housing of the rotary blood pump shown in FIG. 1.

With reference to FIG. 3, the inlet housing portion 14 has a cover 40 that encloses the pumping chamber 18. The inlet 20 is monolithically formed with the cover 40 and protrudes therefrom in a direction of inlet axis 42. As described herein, the inlet axis 42 may be substantially parallel with the central longitudinal axis 26 (shown in FIG. 2). The cover 40 may have a substantially circular shape with at least a portion of the outlet 22 extending tangentially from an outer circumference of the cover 40 in a direction of an outlet axis 44. As described herein, the inlet axis 42 and the outlet axis 44 may be substantially perpendicular to one another. In some examples, the cover 40 may have a first portion of the outlet 22 while the outlet housing portion 16 (shown in FIG. 1) may have a second portion of the outlet 22 such that, when combined, the cover 40 and the outlet housing portion 16 together define the outlet 22. In some examples, the cover 40 may have a circumferential groove 32 (shown in FIG. 5) that interacts with a corresponding projection on the outlet housing portion 16 to position the cover 40 over the outlet housing portion 16.

Figure 4A:
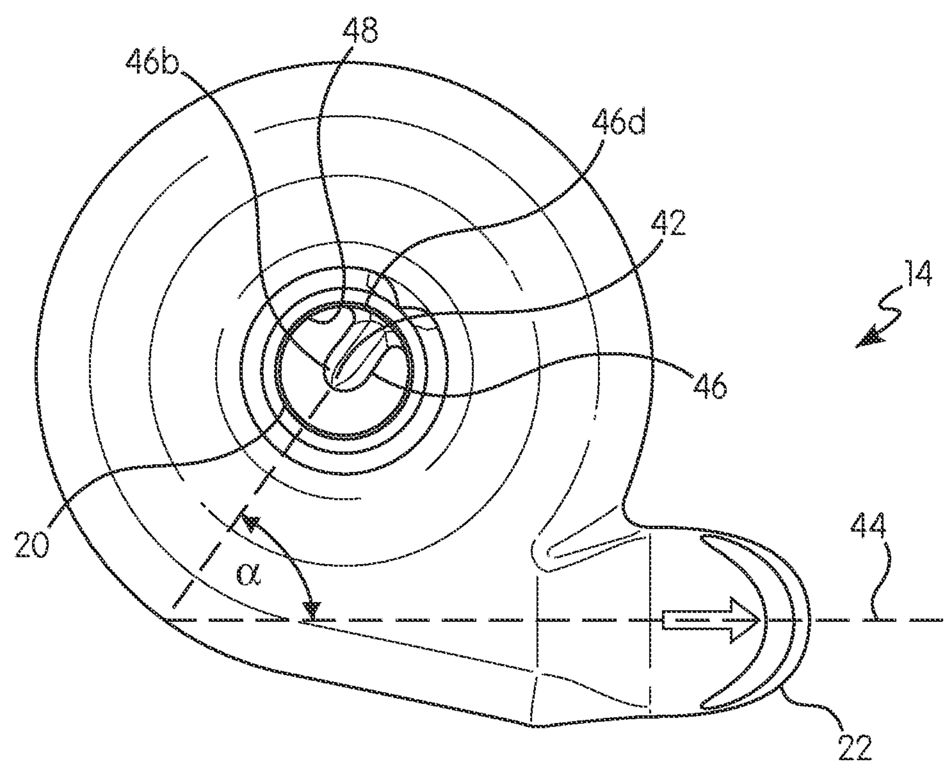
FIG. 4A is a top view of the inlet housing shown in FIG. 3.
Figure 4B:
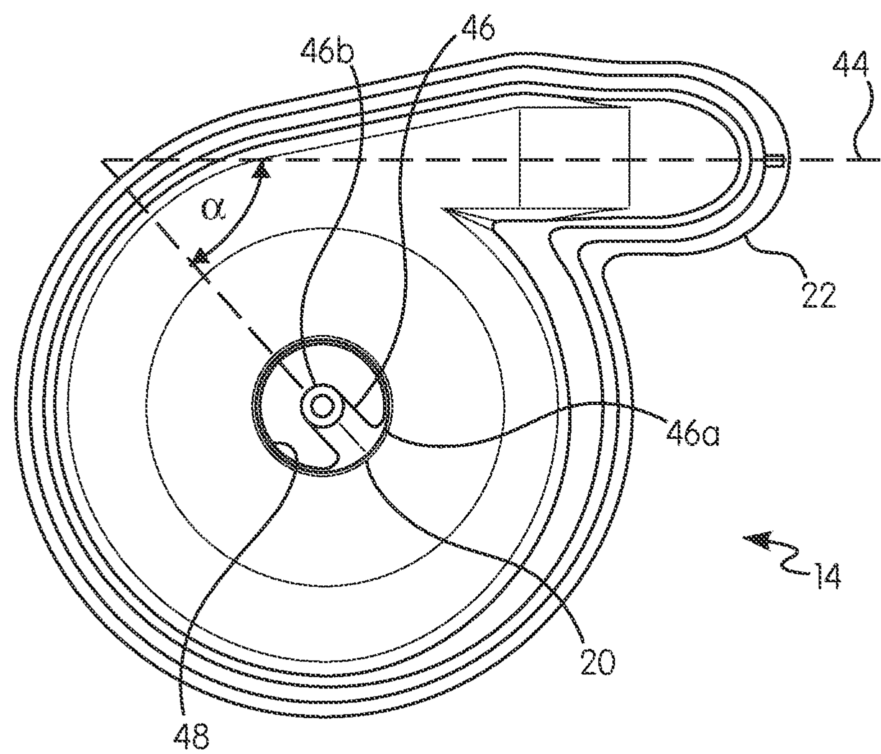
FIG. 4B is a bottom view of the inlet housing shown in FIG. 3.
Figure 4C:
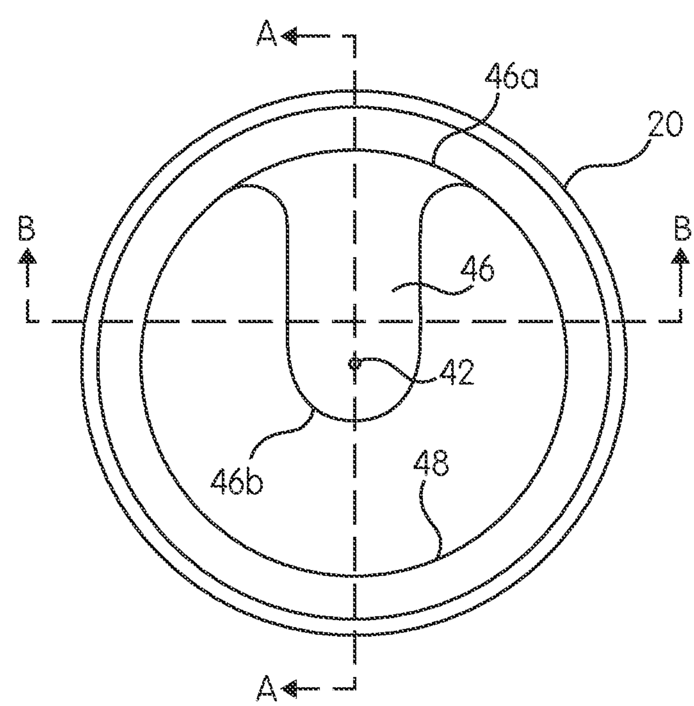
FIG. 4C is a detailed top view of the inlet housing of FIG. 3 showing a strut.

With reference to FIGS. 4A-4B, the inlet housing portion 14 has at least one strut 46 connected to an inner sidewall 48 and extending radially inward toward the inlet axis 42. For example, the strut 46 may be monolithically formed with the inlet housing portion 14, or it may be formed as a separate component that is removably or non-removably connected to the inner sidewall 48 of the inlet 20. The strut 46 has a single connection point with the inner sidewall 48 of the inlet 20 in a circumferential direction around the inlet axis 42 when viewed in a cross-sectional plane perpendicular to the inlet axis 42. With reference to FIG. 4C, the strut 46 has a first radial end **46*a* connected to the inner sidewall 48 of the inlet 20 and a second radial end 46*b* protruding a radially inward from the first radial end 46*a* and toward the inlet axis 42. In some examples, the first radial end 46*a* of the strut 46 is connected to the inner sidewall 48 of the inlet housing portion 14 at a circumferential position about the inlet axis 42 such that a major axis of the strut 46 between the first radial end 46*a* and the second radial end 46*b* and the outlet axis 44 define a predetermined angle $\alpha$ in the cross-sectional plane perpendicular to the inlet axis 42, such as shown in FIGS. 4A-4B. The major axis of the strut 46 between the first radial end 46*a* and the second radial end 46*b* may be coincident with the inlet axis 42. In some examples, the predetermined angle $\alpha$ has an absolute value of about 0° to about 135°, preferably about 15° to about 90°, more preferably about 30° to about 60°, more preferably about 40° to about 50°, more preferably about 43° to about 47°, such as about 45°. The predetermined angle $\alpha$ is based on an orientation of the strut 46 wherein the second radial end 46*b* of the strut 46 extends in a direction toward the outlet axis 44 rather than away from the outlet axis 44, or wherein the second radial end 46*b* of the strut 46 extends in a direction away from the outlet axis 44 rather than toward the outlet axis 44**.

Figure 5A:
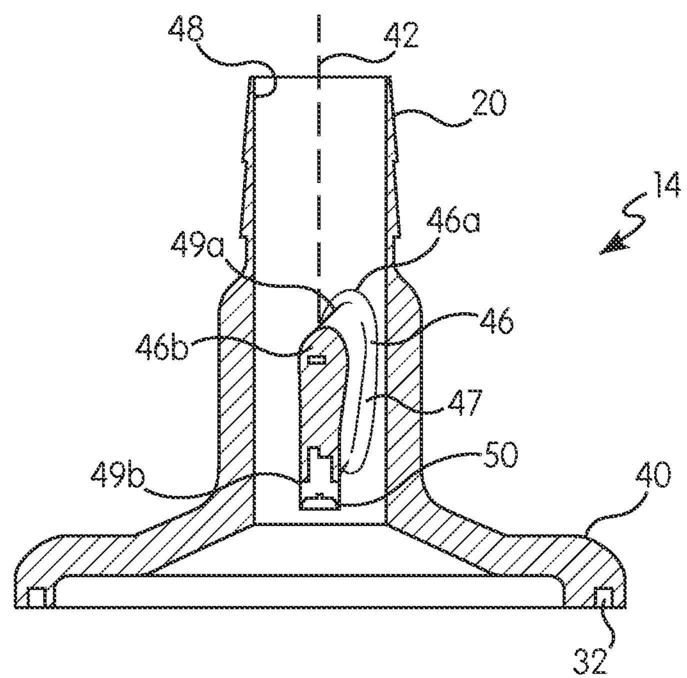
FIG. 5A is a side cross-sectional view of the inlet housing shown in FIG. 3.
Figure 5B:
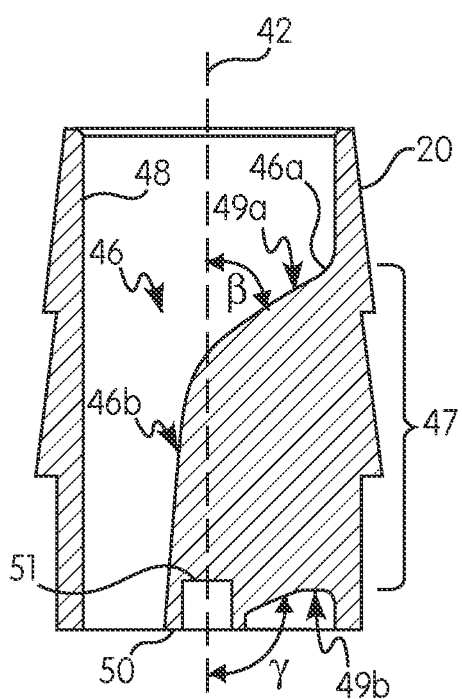
FIG. 5B is a longitudinal cross-sectional view of the strut taken along line A-A in FIG. 4C.
Figure 5C:
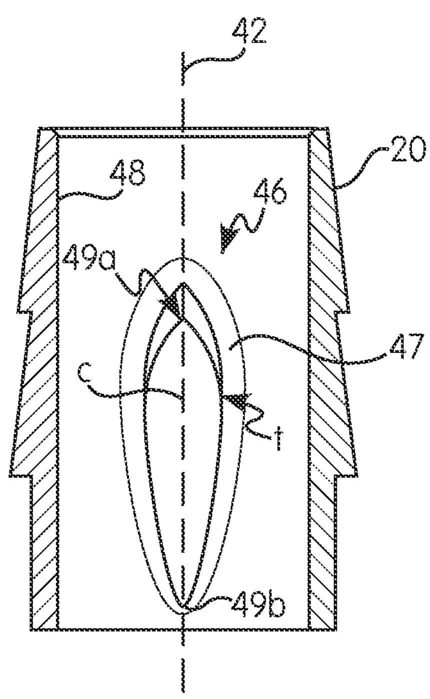
FIG. 5C is a lateral cross-sectional view of the strut taken along line B-B in FIG. 4C.

With reference to FIGS. 5A-5C, the first radial end **46*a* of the strut 46 may be connected to the inner sidewall 48 of the inlet 20 along a connection surface 47 that is substantially parallel with the inlet axis 42. As shown in FIG. 5B, a first axial end 49*a* of the strut 46 is positioned proximate to the inlet 20 (shown in FIG. 3) at an angle $\beta$ relative to the inlet axis 42 when viewed in a cross-sectional plane parallel to the inlet axis 42. The angle $\beta$ is about 15° to about 75°, preferably about 30° to about 60°, more preferably about 40° to about 50°, such as about 45°. The angle $\beta$ is configured to smooth the blood flow around the strut 46 at a leading end of the strut 46 defined by the first axial end 49*a*. A second axial end 49*b* of the strut 46 is positioned opposite the first axial end 49*a*. The second axial end 49*b* of the strut 46 is positioned proximate to the outlet 22 (shown in FIG. 3) at an angle $\gamma$ relative to the inlet axis 42 when viewed in a cross-sectional plane parallel to the inlet axis 42. The angle $\gamma$ is about 15° to about 75°, preferably about 30° to about 60°, more preferably about 40° to about 50°, such as about 45°. The angle $\gamma$ is configured to smooth the blood flow around the strut 46 at a trailing end of the strut 46 defined by the second axial end 49*b*. A terminal portion 50 of the second axial end 49*b* is positioned substantially coaxially with the inlet axis 42. The terminal portion 50 has a bearing support member 51 configured for supporting at least a portion of an axial bearing. As described herein, the axial bearing is configured for supporting the axial load on the impeller 34 directed along the inlet axis 42**.

With reference to FIG. 5C, the strut 46 is desirably shaped to reduce flow stagnation around the strut 46. In some examples, at least a portion of the strut 46 has a teardrop or an airfoil cross-sectional shape. In such examples, the first axial end **49*a* defines a leading edge or end, while the second axial end 49*b* defines a trailing edge or end. The strut 46 may gradually widen from the first axial end 49*a* to a maximum thickness point T, and then gradually narrow from the maximum thickness point T to the second axial end 49*b* along a chord line C. The chord line C is substantially parallel with the inlet axis 42. By varying the position of the maximum thickness point T between the first and second axial ends 49*a*, 49*b*, a pressure profile of the strut 46 can be changed to reduce or eliminate damage to the blood cells within the blood flowing around the strut 46**.

Without intending to be bound by theory, it has been found that positioning the strut 46 at the predetermined angle a, particularly in the range a range of about 45°, reduces or eliminates fluttering or vibration of the strut 46 due to blood flowing through the inlet 20 during pump operation. Such fluttering or vibration of the strut 46 may lead to premature damage or failure of the strut 46, in addition to disrupting the blood flow around the strut 46. While it is possible to reduce such vibration of the strut 46 by making the strut 46 and the inlet housing 14 from a high strength material, such as stainless steel or titanium, positioning the strut 46 at the predetermined angle a allows the strut 46 and the inlet housing 14 to be made from a lower strength material, such as medical grade plastic.

Figure 11:
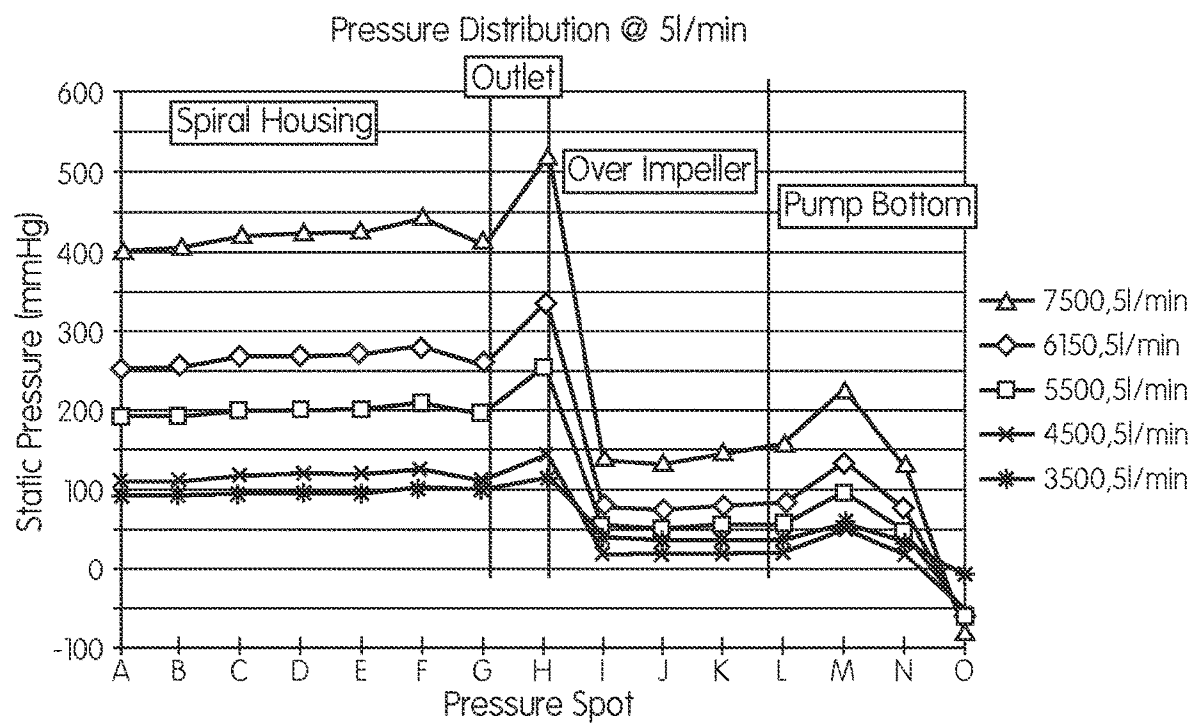
FIG. 11 is a pressure distribution graph showing static pressure at various portions of the inlet housing.
Figure 12:
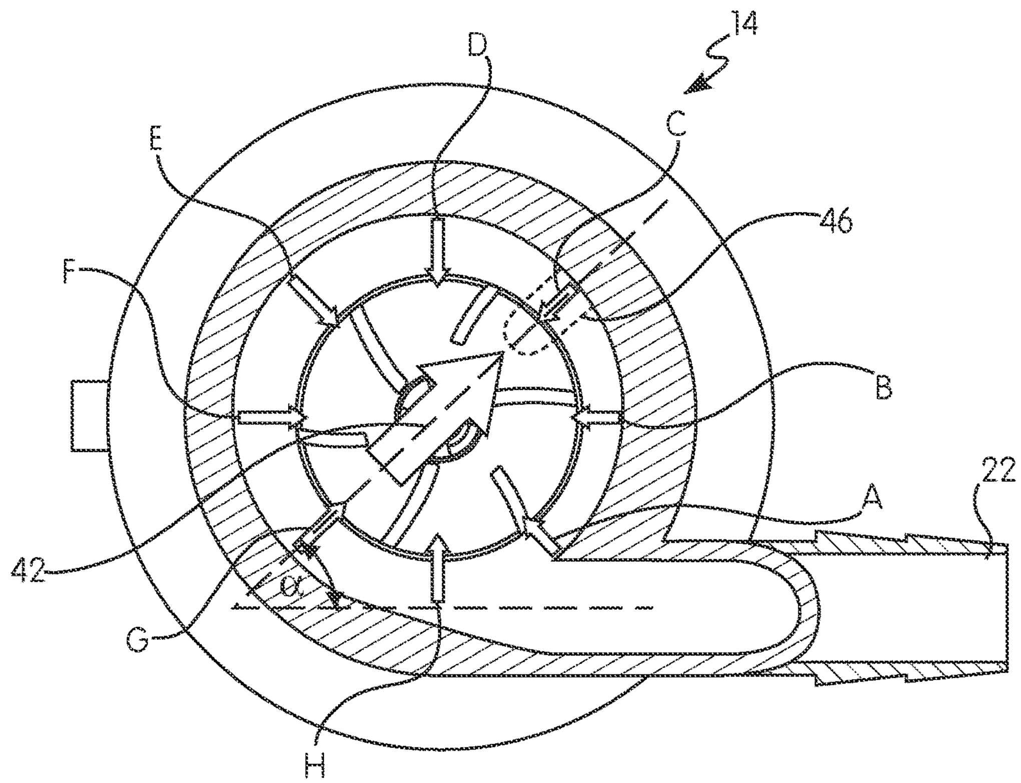
FIG. 12 is a top view of the inlet housing showing a net force diagram based on static pressure values from FIG. 11.

The circumferential position of the strut 46 relative to the inlet axis 42 is chosen to minimize or eliminate static pressure on the strut 46 which may cause a deflection, vibration, or wobble of the strut 46 in a radial direction relative to the inlet axis 42. With reference to FIG. 11, a pressure distribution graph shows a static pressure (in mmHg) at various points of the inlet housing portion 14 (shown in FIG. 3) during pump operation at 5 l/min for various pump rotations per minute (rpm) ranging from 3,500 rpm to 7,500 rpm. Pressure spots A-O in the graph represent various positions on the inlet housing portion 14 at which measurements were taken, with points A-H measuring the static pressure at positions surrounding the inlet axis 42 of the inlet 20 and leading to the outlet 22. By plotting the resultant pressure measurements as force vectors around the inlet axis 42 of the inlet housing 14, it can be seen in FIG. 12 that various circumferential positions on the inner sidewall 48 of the inlet 14 are subject to various pressures. Positioning the strut 46 at a circumferential position about the inlet axis 42 such that a major axis of the strut 46 and the outlet axis 44 define a predetermined angle a in the cross-sectional plane perpendicular to the inlet axis 42 minimizes or eliminates the net side or radial loads on the strut 46 which lead to strut vibration or fluttering. In this manner, damage to blood (such as thrombosis of blood) due to strut vibration or fluttering is reduced or eliminated.

Figure 6:
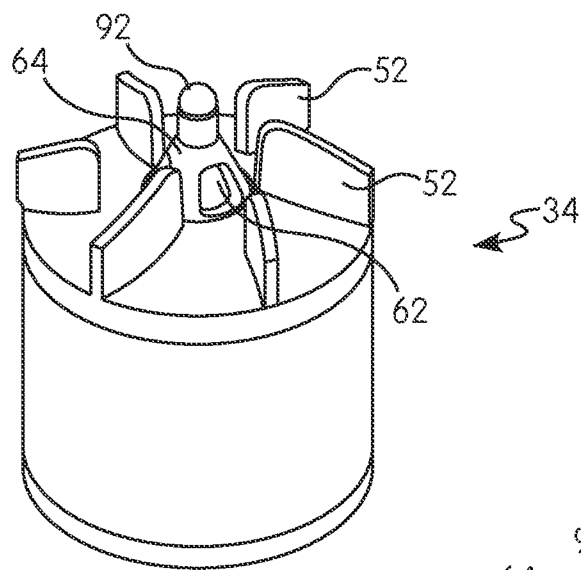
FIG. 6 is a perspective view of an impeller of the rotary blood pump shown in FIG. 1.
Figure 7:
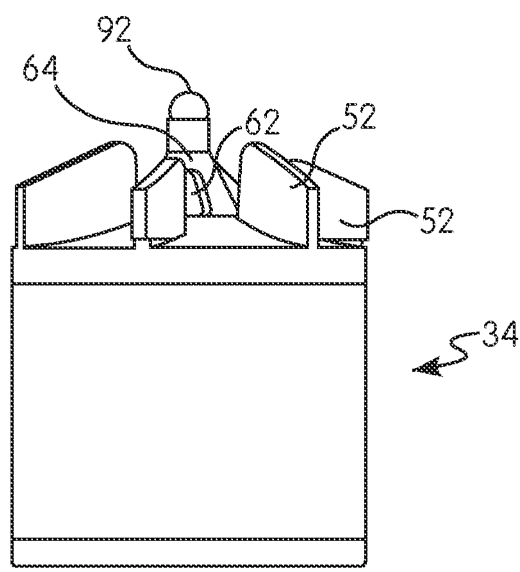
FIG. 7 is a side view of the impeller shown in FIG. 6.
Figure 8:
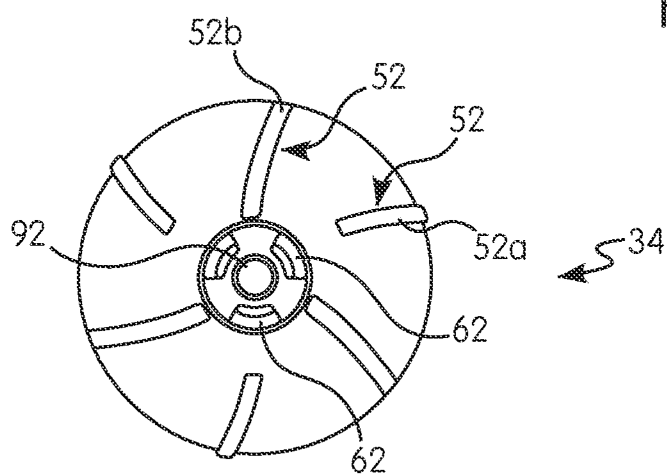
FIG. 8 is a top view of the impeller shown in FIG. 6.

With reference to FIGS. 6-8, the impeller 34 has a generally cylindrical shape that corresponds to the shape of the pumping chamber 18 (shown in FIG. 1). The impeller 34 has a plurality of blades 52 at an upper end thereof that are configured for pumping blood from the inlet 20 toward the outlet 22. In some examples, the impeller 34 has six blades 52 radially spaced apart at equal or unequal angular intervals. The blades 52 may be identical to each other. In some examples, a first subset **52*a* of blades 52 may be different from a second subset 52*b* of blades 52. The first and second subsets 52*a*, 52*b* of blades 52 may be arranged in an alternating manner (see FIG. 8). The blades 52 may be substantially planar. In some examples, the blades 52** may be curved.

Figure 9:
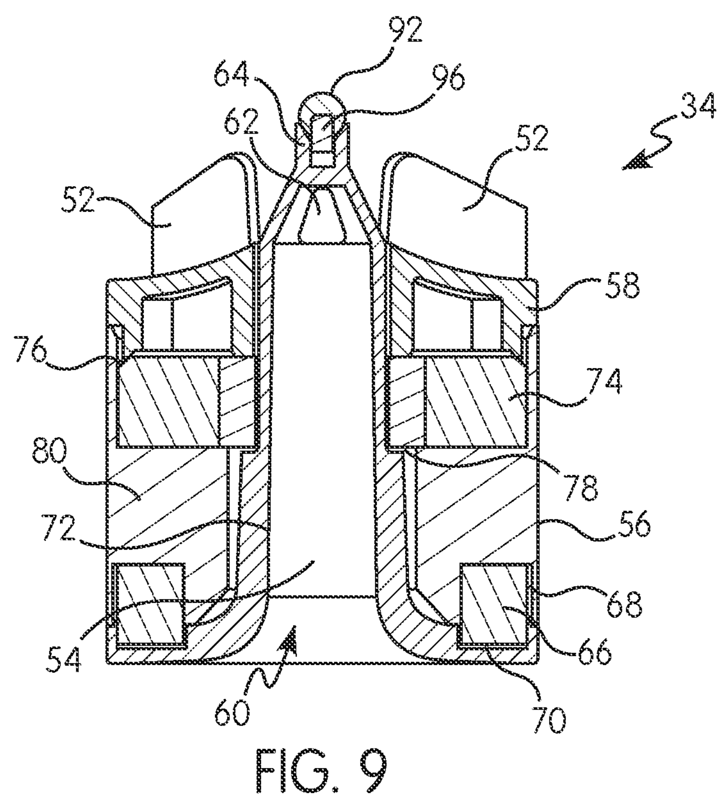
FIG. 9 is a side cross-sectional view of the impeller shown in FIG. 6.
Figure 10:
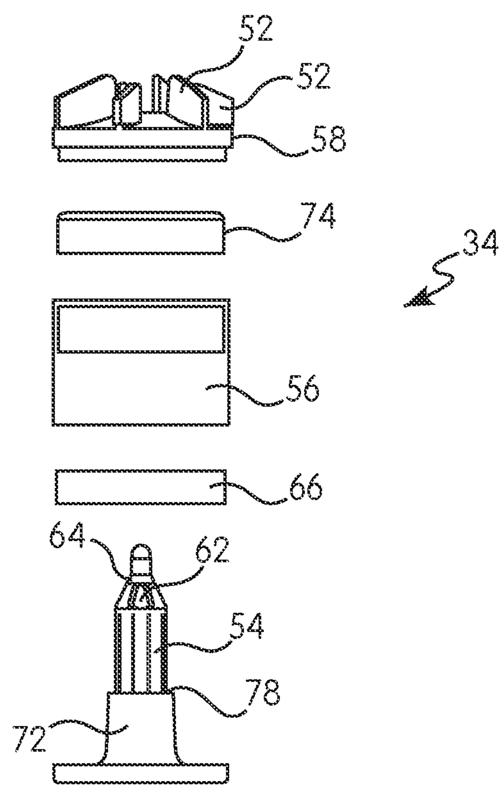
FIG. 10 is an exploded side view of the impeller shown in FIG. 6.

With reference to FIGS. 9-10, the impeller 34 has a hollow central portion 54 surrounded by an outer shell 56. The hollow central portion 54 is disposed within a hollow interior of the outer shell 56. In some examples, the hollow central portion 54 and the outer shell 56 may be formed as separate components which are removably or non-removably connected together. A cap 58 having the blades 52 is positioned on an upper end of the outer shell 56. The cap 58 encloses at least a portion of the hollow interior of the outer shell 56.

With particular reference to FIG. 9, the hollow central portion 54 has at least one passage 60 that is substantially coaxial with the central longitudinal axis 26 (shown in FIG. 1). The at least one passage 60 is in fluid communication with the pumping chamber 18 via one or more openings 62 on an end piece 64 at an upper end of the hollow central portion 54. The at least one passage 60 defines a portion of a secondary flow path, as discussed herein. During operation of the blood pump 10, the impeller 34 delivers a first portion of blood flow from the inlet 20 directly to the outlet 22, and delivers a second portion of the blood flow from the inlet 20 to the outlet 22 via the at least one passage 60 and the one or more openings 62 on the end piece 64. In some examples, the at least one passage 60 is shaped such that its diameter increases in a direction from an upper end to a lower end. In other examples, the at least one passage 60 may have a uniform diameter throughout its length.

With reference to FIGS. 9-10, the impeller 34 has a first bearing magnet 66 at a lower end thereof. The first bearing magnet 66 may be disposed in a first cavity 68 between the hollow central portion 54 and the outer shell 56. In some examples, the first bearing magnet 66 engages a lower skirt 70 that surrounds a central post 72 of the hollow central portion 54. The first bearing magnet 66 is desirably a permanent magnet. In some examples, the first bearing magnet 66 has an annular shape comprised from a single, monolithically formed element. In other examples, the first bearing magnet 66 may be formed from a plurality of discrete magnet segments. For example, the first bearing magnet 66 may have a plurality of arcuate segments having an equal or unequal angular span. The first bearing magnet 66 is configured to magnetically interact with a second bearing magnet associated with the pump housing 12, as described herein.

With continued reference to FIGS. 9-10, the impeller 34 has a rotor magnet 74 axially spaced apart from the first bearing magnet 66. A spacer 80 (shown in FIG. 9) may be provided to axially separate the first bearing magnet 66 from the rotor magnet 74. In some examples, the spacer 80 is monolithically formed with the outer shell 56. In other examples, the spacer 80 is removably or non-removably insertable into a hollow interior of the outer shell 56.

With continued reference to FIGS. 9-10, the rotor magnet 74 may be disposed in a second cavity 76 between the hollow central portion 54 and the outer shell 56. In some examples, the rotor magnet 74 is at least partially supported on a lip 78 extending radially outward from the central post 70 of the hollow central portion 54. The rotor magnet 74 is desirably a permanent magnet. In some examples, the rotor magnet 74 has an annular shape comprised from a plurality of discrete magnet segments. For example, the rotor magnet 74 may have a plurality of arcuate segments having an equal or unequal angular span. In some examples, the rotor magnet 74 has four magnet segments each spanning 9Cf. The magnet segments may form a continuous shape. In some examples, the magnet segments are separate from each other by predetermined spacing.

With reference to FIG. 1, the rotor magnet 74 is configured to magnetically interact with an electromagnetic coil 82 associated with the pump housing 12 to rotatably drive the impeller 34 within the pump housing 12, as described herein. Together, the rotor magnet 74 and the electromagnetic coil 82 define the drive mechanism 36. The rotor magnet 74 is desirably positioned radially opposite the electromagnetic coil 82 such that no net axial force is imparted on the impeller 34 during pump operation. In some examples, any axial force on the impeller 34 due to interaction between the rotor magnet 74 and the electromagnetic coil 82 may be compensated by the bearing mechanism 38, as described herein. The electromagnetic coil 82 is selectively energized to cause the rotor magnet 74 to spin and thereby rotate the impeller 34 about the central longitudinal axis 26. Operation of the electromagnetic coil 82, such as the current and/or voltage it receives, is controlled by a controller 84. The controller 84 is operative for controlling the speed at which the impeller 34 is rotated due to interaction between the rotor magnet 74 and the electromagnetic coil 82.

With continued reference to FIG. 1, the bearing mechanism 38 has a radial bearing 86 having the first bearing magnet 66 associated with the impeller 34 and a second bearing magnet 88 associated with the pump housing 12. The first bearing magnet 66 is coaxial with and magnetically interacts with the second bearing magnet 88 to radially position the impeller 34 within the pumping chamber 18. In particular, the first and second bearing magnets 66, 88 are configured to provide radial stability to the impeller 34 so that the impeller 34 does not contact the sidewall 24 of the pump housing 12 during rotation. The second bearing magnet 88 is desirably a permanent magnet. In some examples, the second bearing magnet 88 has an annular shape comprised from a single, monolithically formed element. In other examples, the second bearing magnet 88 may be formed from a plurality of discrete magnet segments. For example, the second bearing magnet 88 may have a plurality of arcuate segments having an equal or unequal angular span.

In some examples, the first bearing magnet 66 and the second bearing magnet 88 are positioned, for example coaxially arranged and axially offset, such that a net axial thrust force urges the impeller 34 in a direction toward the inlet 20. The net axial thrust force may be generated due to an axial offset between the first bearing magnet 66 and the second bearing magnet 88, a difference in magnetic properties, such as magnetic strength, between the first bearing magnet 66 and the second bearing magnet 88, or a combination thereof. In some examples, the axial offset between the first bearing magnet 66 and the second bearing magnet 88 may be such that the impeller 34 is urged in a direction along the central longitudinal axis 26 toward the inlet 20 with an axial thrust force of sufficient magnitude to axially support the weight of the impeller 34 during operation against an axial bearing 90, and without the engagement between the components of the axial bearing 90 which may generate heat of a degree that may lead to excessive heating of the blood (such as above 42° C.) that flows around the axial bearing 90 that could cause damage to the blood cells.

With continued reference to FIG. 1, the axial bearing 90 is a mechanical bearing that is configured to take up the axial thrust force due to magnetic interaction between the first bearing magnet 66 and the second bearing magnet 88. The axial bearing 90 has a first bearing element 92 associated with the impeller 34 and a second bearing element 94 associated with the strut 46 connected to the inlet housing portion 14. In some examples, the first bearing element 92 is ball-shaped and the second bearing element 94 is cup-shaped to receive at least a portion of the ball-shaped first bearing element 92. Alternatively, the second bearing element 94 is ball-shaped and the first bearing element 92 is cup-shaped to receive at least a portion of the ball-shaped second bearing element 94. The first bearing element 92 and the second bearing element 94 are shaped to allow a slight pivoting movement about the axial bearing 90 to allow for radial centering of the impeller 34 during pump operation. The axial thrust force generated by the magnetic interaction between the first bearing magnet 66 and the second bearing magnet 88 is transferred to the pump housing 12 by way of the axial bearing 90 and the strut 46.

With reference to FIG. 9, the first bearing element 92 may be a ball supported on a post 72 connected to the end piece 64 of the hollow central portion 54 of the impeller 34. In some examples, the first bearing element 92 is a jewel bearing, such as a ruby ball.

With reference to FIG. 5, the second bearing element 94 may be a cup that is formed at the terminal end 50 of the strut 46. The second bearing element 94 may be removably or non-removably connected to the terminal end 50 of the strut 46. In some examples, the second bearing element 94 is made from a ceramic material.

In operation, the rotor magnet 74 magnetically interacts with an electromagnetic coil 82 associated with the pump housing 12 to rotatably drive the impeller 34 within the pump housing 12. Blood flowing through the inlet 20 flows around the strut 46 and washes over the axial bearing 90, thereby cooling the axial bearing 90. As described herein, the strut 46 is desirably shaped to reduce flow stagnation around the strut 46, as well as eliminate fluttering or vibration as the blood flows around the strut 46.

As the blood enters the pumping chamber 18 through the inlet 20, the impeller blades 52 pump the blood in a radially outward direction relative to the inlet axis 42 to direct a first portion of the blood flow comprising a majority of the blood entering the pumping chamber 18 toward the outlet 22. A second portion of the blood flow passes through a radial gap 96 between the sidewall 24 of the pumping chamber 12 and the outer surface of the cylindrical portion of the impeller 34 as a secondary fluid path. This secondary flow path allows blood to pass to the bottom 98 of the pumping chamber 12. In some examples, the bottom 98 of the pumping chamber 12 may have a deflector 100 to direct blood flow in the secondary flow path to the at least one passage 60. The blood in the secondary flow path then flows axially through the at least one passage 60 in a direction toward the inlet 20 to the bottom of the axial bearing 90 through the one or more openings 62 on the end piece 64 of the hollow central portion 54 of the impeller 34. This reduces blood stagnation and incidence of thrombus formation. The blood flow from the secondary flow path then enters the pumping chamber 18 before exiting the pumping chamber 18 through the outlet 22.

While examples of a rotary blood pump are provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A centrifugal blood pump comprising:

a housing having a pumping chamber, an inlet with an inlet axis, and an outlet with an outlet axis, the inlet and the outlet being in fluid communication with the pumping chamber;

an impeller rotatably disposed within the pumping chamber;

at least one bearing supporting the impeller within the pumping chamber; and a strut connected to the housing at the inlet to support at least a portion of the bearing mechanism, wherein the strut is fixed directly to an inner sidewall of the housing at a fixation point at a circumferential position about the inlet axis such that a major axis of the strut and the outlet axis define a predetermined angle in a cross-sectional plane perpendicular to the inlet axis, wherein a first axial end of the strut proximate the inlet extends from the inner sidewall of the housing towards the inlet axis at an angle of 15° to 75° relative to the inlet axis.

2. The centrifugal blood pump of claim 1, wherein the strut extends radially into the inlet from the fixation point with the housing in the cross-sectional plane perpendicular to the inlet axis.

3. The centrifugal blood pump of claim 2, wherein the predetermined angle is 15° to 75°.

4. The centrifugal blood pump of claim 1, wherein at least a portion of the strut has a teardrop cross-sectional shape.

5. The centrifugal blood pump of claim 1, wherein the impeller has at least one passage defining a secondary flow path.

6. The centrifugal blood pump of claim 5, wherein the at least one passage is substantially perpendicular to the outlet axis.

7. The centrifugal blood pump of claim 5, wherein, during operation of the blood pump, the impeller delivers a first portion of blood flow from the inlet directly to the outlet, and delivers a second portion of the blood flow from the inlet to the outlet via the at least one passage.

8. The centrifugal blood pump of claim 1, wherein the at least one bearing comprises:

a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first component associated with the impeller and a second component connected to the strut.

9. The centrifugal blood pump of claim 8, wherein the first component is ball-shaped and the second component is cup-shaped to receive at least a portion of the ball-shaped first component or the second component is ball-shaped and the first component is cup-shaped to receive at least a portion of the ball-shaped second component.

10. The centrifugal blood pump of claim 8, wherein the first component is a jewel bearing.

11. The centrifugal blood pump of claim 8, wherein the second component is made from a ceramic material.

12. The centrifugal blood pump of claim 8, wherein the first permanent magnet is axially offset relative to the second permanent magnet by a predetermined distance to urge the impeller in a direction toward the inlet with a predetermined axial force.

13. The centrifugal blood pump of claim 1, further comprising a motor mechanism for rotating the impeller within the pumping chamber, the motor mechanism having a permanent magnet rotor associated with the impeller and an electromagnetic coil stator associated with the housing.

14. A centrifugal blood pump comprising:

a housing having a pumping chamber, an inlet with an inlet axis, and an outlet with an outlet axis, the inlet and the outlet being in fluid communication with the pumping chamber;

an impeller rotatably disposed within the pumping chamber and having at least one passage defining a secondary flow path, wherein the at least one passage provides at least a first fluid pathway that extends in a direction substantially parallel to the inlet axis, the first fluid pathway extending linearly from an inlet in fluid communication with the pumping chamber to an outlet at a lower end of the impeller, an entirety of the first fluid pathway extending linearly from the inlet to the outlet; and at least one bearing supporting the impeller within the pumping chamber;

wherein, during operation of the blood pump, the impeller delivers a first portion of blood flow from the inlet directly to the outlet, and delivers a second portion of the blood flow from the inlet to the outlet via the first fluid pathway in the at least one passage.

15. The centrifugal blood pump of claim 14, wherein the first fluid pathway defining the secondary flow path is substantially perpendicular to the outlet axis.

16. The centrifugal blood pump of claim 14, further comprising a strut connected to the housing at the inlet to support at least a portion of the bearing mechanism, wherein the strut is connected to the housing at a circumferential position about the inlet axis such that a major axis of the strut and the outlet axis define a predetermined angle in a cross-sectional plane perpendicular to the inlet axis.

17. The centrifugal blood pump of claim 16, wherein the strut has a single connection point with the housing in the cross-sectional plane perpendicular to the inlet axis.

18. The centrifugal blood pump of claim 16, wherein the predetermined angle is 15° to 75°.

19. The centrifugal blood pump of claim 14, wherein the at least one bearing comprises:

a radial bearing having a first permanent magnet associated with the impeller and a second permanent magnet associated with the housing, the first permanent magnet magnetically interacting with the second permanent magnet to radially position the impeller within the pumping chamber; and an axial bearing comprising a first component associated with the impeller and a second component connected to the strut.

20. The centrifugal blood pump of claim 19, wherein the first permanent magnet is axially offset relative to the second permanent magnet by a predetermined distance to urge the impeller in a direction toward the inlet with a predetermined axial force.

* * * * *